United States Patent [19]

Neises

[11] 4,252,018

[45] Feb. 24, 1981

[54] GRAIN SAMPLER WITH HOUSING

[76] Inventor: Mark M. Neises, 708 E. 18th St., Wichita, Kans. 67214

[21] Appl. No.: 41,476

[22] Filed: May 22, 1979

[51] Int. Cl.³ .......................... G01N 1/12; G01N 1/18
[52] U.S. Cl. .................................... 73/421 A; 73/424
[58] Field of Search .................. 73/421 R, 421 A, 424

[56] References Cited

U.S. PATENT DOCUMENTS 3,280,635  10/1966  Cochet ................................... 73/424

FOREIGN PATENT DOCUMENTS 34588  2/1886  Fed. Rep. of Germany ............ 73/424

Primary Examiner—S. Clement Swisher

[57] ABSTRACT

An automatic grain sampling device including a paddle wheel with paddles rotated by the force of grain on a conveyor against the paddles and a sampling receptacle attached to the paddle wheel, a hopper, apparatus for controlling the size of sample dumped, and proportioner apparatus to control the proportion of the sample retained.

11 Claims, 8 Drawing Figures

GRAIN SAMPLER WITH HOUSING

BACKGROUND OF THE INVENTION

1. Field of the Invention

This invention provides for an in-house grain sampler. More specifically, this invention provides for an in-house grain sampler which is automatically driven by the flow of grain on a conveyor belt.

2. Description of Prior Art

U.S. Pat. No. 665,620 discloses an automatic tailings sampler; and U.S. Pat. No. 4,133,210 teaches a sampling apparatus. U.S. Pat. Nos. 3,280,635 and 3,503,266 disclose an automatic sampler with scooping wheel, and a grain sampler device, respectively. None of these U.S. patents teach the in-house grain sampler of this invention.

SUMMARY OF THE INVENTION

It is therefore an object of this invention to provide for an in-house grain belt sampler.

Broadly, this invention provides for an improved automatic grain sampling device including a paddle wheel in a housing and a continuously moving conveyor belt advancing a continuous stream of grain, the paddle wheel being so positioned relative to the grain stream such that the paddles engage the grain stream to drive or rotate the wheel. The improvement comprises a receptacle carried by the wheel operative to retrieve periodically and automatically a sample of grain from the moving stream; a hopper means cooperating with the receptacle and into which the receptacle automatically dumps the grain; means for controlling the size of the sample dumped; and proportioner means operative to receive the sample and to size the sample.

DETAILED DESCRIPTION OF THE INVENTION

Figure 1:
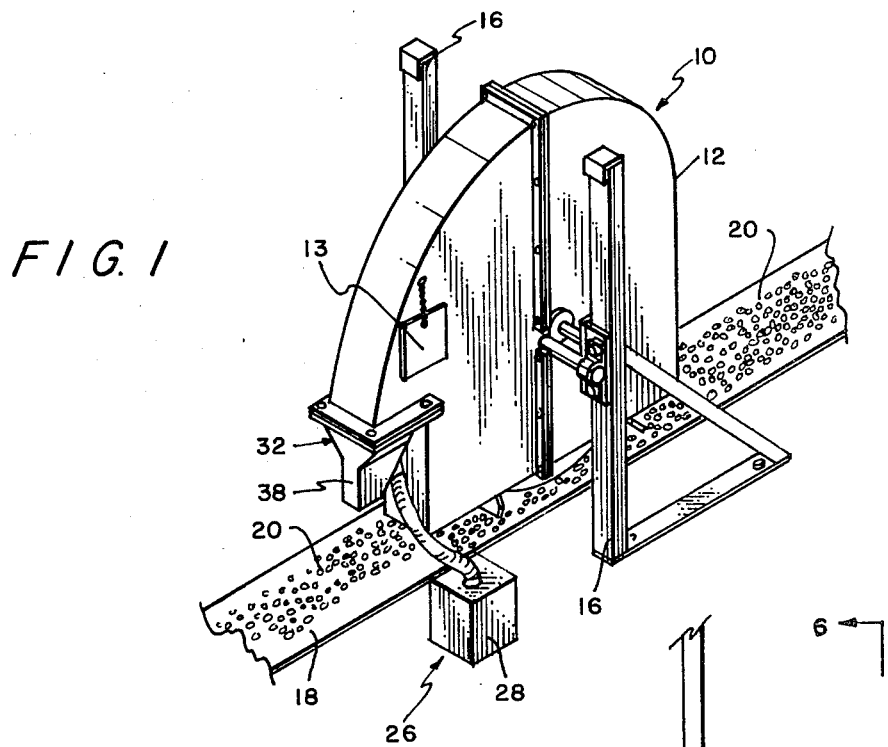
FIG. 1 is a perspective view of the in-house grain sampler.
Figure 2:
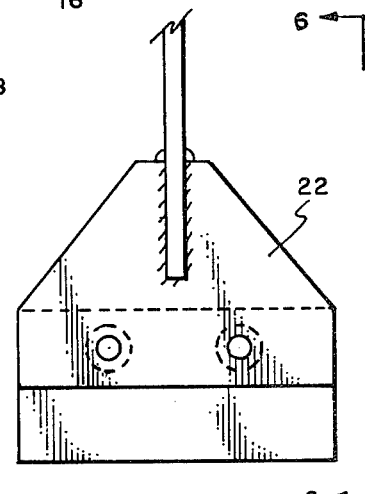
FIG. 2 is an enlarged front elevational view of a paddle.
Figure 3:
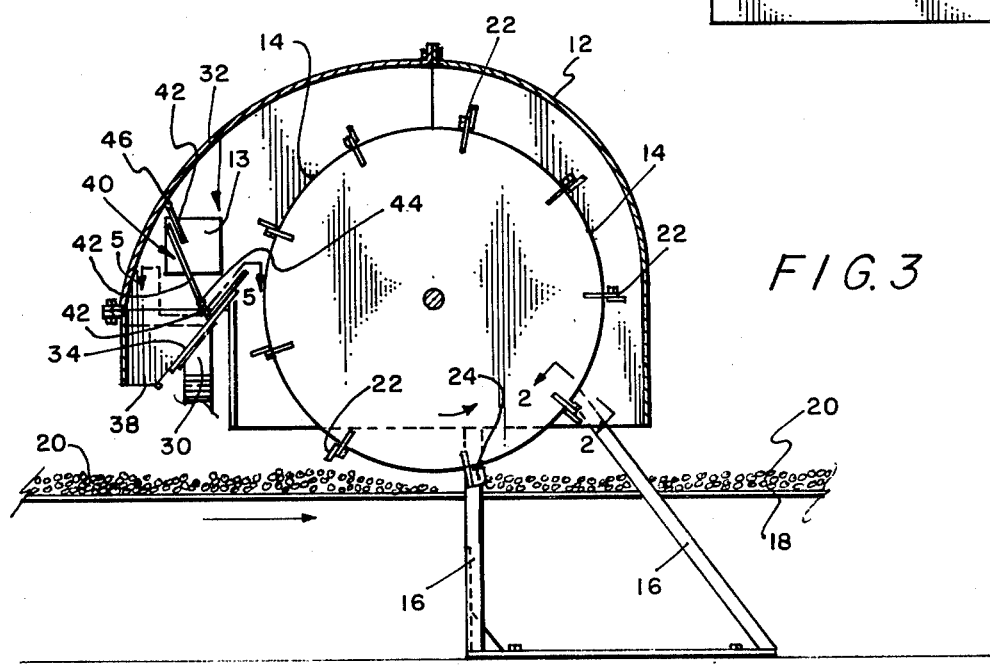
FIG. 3 is a vertical side elevational view of the in-house grain sampler.
Figure 4:
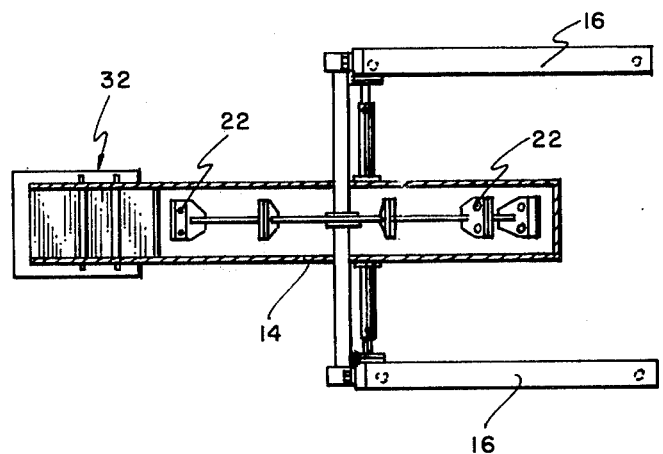
FIG. 4 is a top plane view of the in-house grain sampler having the housing removed.
Figure 5:
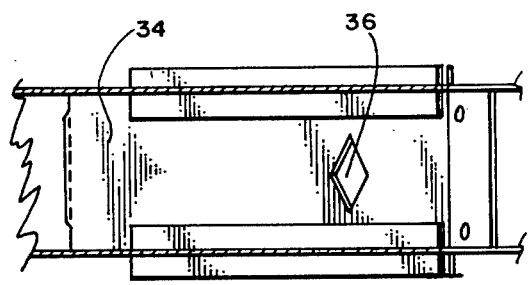
FIG. 5 is a top plane view of the slide taken along the plane of line 5—5 in FIG. 3.
Figure 6:
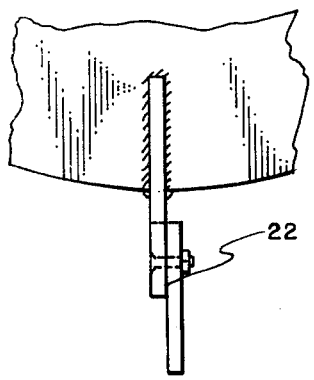
FIG. 6 is a side elevational view of the paddle taken along the plane of line 6—6 in FIG. 2.
Figure 7:
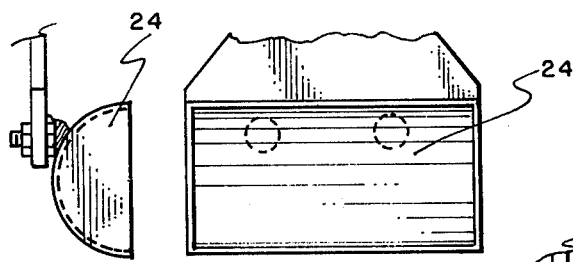
FIG. 7 is a combination front and side elevational view of the cup-like receptacle.
Figure 8:
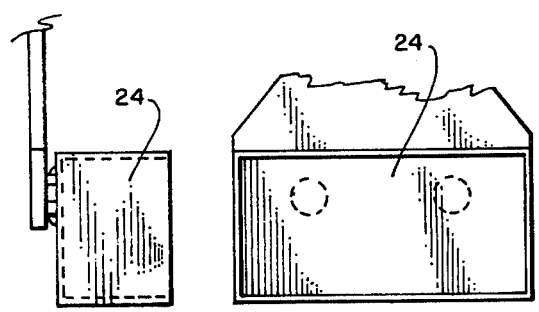
FIG. 8 is a combination front and side elevational view of the box-like receptacle.

Referring in detail now to the drawings, wherein like reference numerals represent similar parts, there is seen an in-house grain belt sampler, generally illustrated as 10, having a housing 12 with a door 13, a paddle wheel 14 rotating in the housing 12, a frame 16, and a conveyor belt 18 advancing a continuous stream of grain 20. Paddle wheel 14 has a plurality of paddles 22 attached thereto for engaging the grain stream to drive or rotate the paddle wheel 14. A box-like or cup-like receptacle 24 is also attached to the paddle wheel 14 which periodically and automatically retrieves a sample of grain 20 from the moving grain stream. Hopper means, generally illustrated as 26, cooperates with receptacle 24 such as to facilitate the dumping of grain 20 therein. Hopper means 26 includes a sample container 28 and a conduit 30. Means for controlling the size of sample dumped, generally illustrated as 32, is attached to the housing 12 and includes a slide 34 having an aperture 36; the slide 34 is movable relative to the conduit 30 of hopper means 26 in order to effectively change the size of the aperture 36 to control the sample size as the grain 20 slides down the slide 34 by the force of gravity. Means for controlling 32 also includes an overflow spout 38 operative to direct excessive grain 20 sample (not falling through aperture 36 and into container 28 via conduit 30) back to the grain 20 stream. A proportioner means, generally illustrated as 40, is operative to receive and size the grain sample; it cooperates with the control means 32 to direct the sized sample to hopper means 26 and to retard and direct excess grain 20 back to the grain 20 stream. Proportioner means 40 comprises a plurality of baffle or webs 42 movable from one fixed position to another fixed position. The plurality of webs 42 preferably comprises a pair of webs 42 pivoting about a common point 44, and a third web 42 pivoting about point 46 and cooperating with one of the pair of webs 42 (see FIG. 3). The other of the pair of webs 42 is operative to engage the grain 20 to retard the flow of same to encourage the sampling of the correct amount.

With continuing reference to the drawings for operation of the invention, a continuous stream of grain 20 moves on conveyor belt 18. Grain 20 engages paddles 22 to rotate the wheel 14. Receptacle 24 periodically and automatically retrieves a sample of grain 20 and dumps it into slide 34 of control means 32. Slide 34 having aperture 36 is movable relative to the conduit 30 of hopper means 26 in order to position the aperture 36 over conduit 30. The sample size is predetermined, so if a large sample is desired, slide 34 would be positioned such as to expose a large part of aperture 36 over conduit 30, and vice versa if a small sample is desired. Webs 42 pivoting about point 44 can be set such as to have the lower web 42 (which engages the grain 20 as gravity pulls it down the slide 34 toward overflow spout 38) retard the flowing of the grain 20 down slide 34 in order to give the desired amount of grain 20 a chance to flow through aperture 36 and into the container 28 via conduit 30. All webs 42 can be manually set at a desired angle through door 13. The top web 42, pivoting about point 46, cooperates with the middle web 42 to prevent the weight of the grain 20 against the lower web 42 from turning the lower web 42 in a clockwise direction about point 44 to place same out of position (see FIG. 3). Once the webs 42 are out of position, sampling becomes ineffective because the desired sample size grain 20 is not given time to fall through aperture 36. Any grain 20 not falling through aperture 36 is directed back to the grain stream through overflow spout 38.

Changes may be made in the construction and arrangement of the parts or elements of the embodiments as disclosed herein without departing from the spirit or scope of the invention.

I claim:

1. In an automatic grain sampling device including a paddle wheel in a housing and a continuously moving conveyor belt advancing a continuous stream of grain, the paddle wheel being so positioned relative to the grain stream such that the paddles engage the grain stream to drive or rotate the wheel, the improvement comprising a receptacle carried by the wheel operative to retrieve periodically and automatically a sample of grain from said moving stream; hopper means cooperating with the receptacle and into which the receptacle automatically dumps the grain, and means for controlling the size of sample dumped cooperating with the receptacle and attached to said housing.

2. The device of claim 1 wherein said receptacle is cup-like.

3. The device of claim 1 wherein said receptacle is box-like.

4. The device of claim 1 wherein the control means comprises a slide having an aperture, said slide being movable relative to said hopper means effective to change the size of the aperture to effectively control the sample size.

5. The device of claim 4 in which the control means includes an overflow spout operative to direct excessive grain sample back to the grain stream.

6. The device of claim 5 wherein said hopper means comprises a conduit in communication with said aperture, and a sample container attached to and in communication with said conduit.

7. The device of claim 4 additionally including a proportioner means cooperating with said control means to direct the sized sample to said hopper means and to direct excess grain back to the grain stream.

8. In a grain sampler of the type utilizing a paddle wheel including a grain receptacle, all driven by an advancing grain stream, the improvement comprising a proportioner means operative to receive the sample and to size the sample, and control means cooperating with the proportioner means to direct the sized sample to a sample hopper and to direct excess grain back to the grain stream.

9. The device of claim 8 wherein said proportioner means comprising an adjustable baffle means to retard the flow of excess grain back to the grain stream.

10. The device of claim 9 wherein said baffle means comprises a plurality of cooperating webs movable from one fixed position to another fixed position.

11. The device of claim 10 wherein said plurality of cooperating webs comprises a pair of webs connecting and pivoting about a common point, a third web pivoting at another point and cooperating with one of said pair of webs, the other of said pair of webs is operative to engage said grain to retard the flow of same to encourage the sampling of the correct amount.

* * * * *